(12) United States Patent
Tan et al.

(10) Patent No.: US 11,896,233 B2
(45) Date of Patent: Feb. 13, 2024

(54) CIRCULAR STAPLING DEVICE

(71) Applicant: Covidien LP, Mansfield, MA (US)

(72) Inventors: Yuandong Tan, Shanghai (CN); Xiliang Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 276 days.

(21) Appl. No.: 17/611,396

(22) PCT Filed: May 31, 2019

(86) PCT No.: PCT/CN2019/089545
§ 371 (c)(1),
(2) Date: Nov. 15, 2021

(87) PCT Pub. No.: WO2020/237631
PCT Pub. Date: Dec. 3, 2020

(65) Prior Publication Data
US 2022/0211381 A1 Jul. 7, 2022

(51) Int. Cl.
*A61B 17/115* (2006.01)
*A61B 90/00* (2016.01)
*A61B 17/00* (2006.01)

(52) U.S. Cl.
CPC .......... *A61B 17/1155* (2013.01); *A61B 90/03* (2016.02); *A61B 2017/00367* (2013.01); *A61B 2090/037* (2016.02)

(58) Field of Classification Search
CPC ................ A61B 90/03; A61B 17/1155; A61B 2090/037; A61B 2017/00367
USPC .......................................... 227/179.1, 180.1
See application file for complete search history.

(56) References Cited

U.S. PATENT DOCUMENTS

| | | | |
|---|---|---|---|
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Interational Search Report dated Feb. 7, 2020, issued in corresponding International Appln. No. PCT/CN2019/089545, 2 pages.

(Continued)

*Primary Examiner* — Dariush Seif
(74) *Attorney, Agent, or Firm* — Carter, DeLuca & Farrell LLP

(57) ABSTRACT

A circular stapling device includes a manually operated trigger (24) that is adapted to allow staple formation to occur prior to cutting of tissue during a single actuation of the firing trigger (24). The stapling device (10) minimizes stretching and movement of tissue during staple formation to improve staple formation. The stapling device (10) also reduces the amount of force required to move the firing trigger (24) through a firing stroke by separating the staple formation and tissue cutting functions of the stapling device (10) to reduce stress on a clinician's hand during actuation of the stapling device (10).

20 Claims, 9 Drawing Sheets

(56) References Cited

U.S. PATENT DOCUMENTS

| | | |
|---|---|---|
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |

(56) References Cited

U.S. PATENT DOCUMENTS

| | | |
|---|---|---|
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |

(56) References Cited

U.S. PATENT DOCUMENTS

| | | |
|---|---|---|
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |

(56) References Cited

U.S. PATENT DOCUMENTS

| | | |
|---|---|---|
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1* | 7/2013 | Milliman ............ A61B 17/1155 227/180.1 |
| 2013/0181036 A1* | 7/2013 | Olson ................. A61B 17/068 227/176.1 |
| 2013/0193190 A1 | 8/2013 | Carter et al. |
| 2013/0200131 A1* | 8/2013 | Racenet ............. A61B 17/1155 227/180.1 |
| 2013/0206816 A1 | 8/2013 | Penna |
| 2013/0240597 A1 | 9/2013 | Milliman et al. |
| 2013/0274771 A1* | 10/2013 | Williams ............ A61B 17/072 606/153 |
| 2013/0277411 A1 | 10/2013 | Hodgkinson et al. |
| 2013/0284792 A1 | 10/2013 | Ma |
| 2014/0008413 A1* | 1/2014 | Williams ............ A61B 17/1155 227/179.1 |
| 2014/0046352 A1 | 2/2014 | Reboa et al. |
| 2014/0158747 A1 | 6/2014 | Measamer et al. |

(56) References Cited

U.S. PATENT DOCUMENTS

| | | | |
|---|---|---|---|
| 2014/0197225 A1* | 7/2014 | Penna | A61B 17/068 227/179.1 |
| 2014/0239046 A1* | 8/2014 | Milliman | A61B 17/07292 227/176.1 |
| 2014/0252062 A1* | 9/2014 | Mozdzierz | A61B 17/1155 227/175.1 |
| 2014/0284370 A1 | 9/2014 | Sahin | |
| 2015/0014393 A1* | 1/2015 | Milliman | A61B 17/1155 227/176.1 |
| 2015/0083772 A1 | 3/2015 | Miller et al. | |
| 2015/0129636 A1* | 5/2015 | Mulreed | A61B 17/115 227/177.1 |
| 2015/0173763 A1 | 6/2015 | Liu | |
| 2015/0190133 A1* | 7/2015 | Penna | A61B 17/068 227/175.2 |
| 2015/0209045 A1 | 7/2015 | Hodgkinson et al. | |
| 2016/0000428 A1* | 1/2016 | Scirica | A61B 17/072 227/180.1 |
| 2016/0007999 A1* | 1/2016 | Latimer | A61B 17/1155 227/177.1 |
| 2016/0361057 A1* | 12/2016 | Williams | A61B 17/068 |
| 2017/0128068 A1 | 5/2017 | Zhang et al. | |
| 2018/0125486 A1* | 5/2018 | Guerrera | A61B 17/1155 |
| 2018/0125495 A1* | 5/2018 | Sgroi, Jr. | A61B 17/07207 |
| 2018/0317920 A1* | 11/2018 | Guerrera | A61B 17/1155 |
| 2018/0353186 A1* | 12/2018 | Mozdzierz | A61B 17/072 |
| 2019/0105051 A1 | 4/2019 | Swayze et al. | |
| 2019/0216462 A1* | 7/2019 | Milliman | A61B 17/1155 |
| 2019/0321046 A1* | 10/2019 | Williams | A61B 17/1155 |
| 2021/0212693 A1* | 7/2021 | Joyce | A61B 17/1155 |
| 2022/0211381 A1* | 7/2022 | Tan | A61B 90/03 |

FOREIGN PATENT DOCUMENTS

| | | | |
|---|---|---|---|
| CN | 103371861 A | 10/2013 | |
| CN | 103919586 A | 7/2014 | |
| CN | 104039244 A | 9/2014 | |
| CN | 104042288 A | 9/2014 | |
| CN | 104367360 A | 2/2015 | |
| CN | 104853684 A | 8/2015 | |
| DE | 1057729 B | 5/1959 | |
| DE | 3301713 A1 | 7/1984 | |
| EP | 0152382 A2 | 8/1985 | |
| EP | 0173451 A1 | 3/1986 | |
| EP | 0190022 A2 | 8/1986 | |
| EP | 0282157 A1 | 9/1988 | |
| EP | 0503689 A2 | 9/1992 | |
| EP | 1354560 A2 | 10/2003 | |
| EP | 1671597 A1 | 6/2006 | |
| EP | 2138118 A2 | 12/2009 | |
| EP | 2168510 A1 | 3/2010 | |
| EP | 2238926 A2 | 10/2010 | |
| EP | 2524656 A2 | 11/2012 | |
| EP | 2614785 A2 | 7/2013 | |
| EP | 2623042 A2 | 8/2013 | |
| EP | 2754398 A2 | 7/2014 | |
| EP | 2823774 A2 | 1/2015 | |
| EP | 3023077 A1 | 5/2016 | |
| EP | 3123954 A2 | 2/2017 | |
| EP | 3318200 A1 | 5/2018 | |
| EP | 3378411 A1 | 9/2018 | |
| EP | 3412225 A1 | 12/2018 | |
| EP | 3549545 A2 | 10/2019 | |
| FR | 1136020 A | 5/1957 | |
| FR | 1461464 A | 2/1966 | |
| FR | 1588250 A | 4/1970 | |
| FR | 2443239 A1 | 7/1980 | |
| GB | 1185292 A | 3/1970 | |
| GB | 2016991 A | 9/1979 | |
| GB | 2070499 A | 9/1981 | |
| JP | 2004147969 A | 5/2004 | |
| JP | 2013138860 A | 7/2013 | |
| JP | 2014133128 A | 7/2014 | |
| JP | 2018521787 A | 8/2018 | |
| JP | 2018158108 A | 10/2018 | |
| JP | 2019520921 A | 7/2019 | |
| KR | 100769681 B1 | 10/2007 | |
| NL | 7711347 A | 4/1979 | |
| SU | 1509052 A1 | 9/1989 | |
| WO | 8706448 A1 | 11/1987 | |
| WO | 8900406 A1 | 1/1989 | |
| WO | 9006085 A1 | 6/1990 | |
| WO | 9835614 A1 | 8/1998 | |
| WO | 0154594 A1 | 8/2001 | |
| WO | 02080781 A2 | 10/2002 | |
| WO | 2004032766 A2 | 4/2004 | |
| WO | 2004047654 A2 | 6/2004 | |
| WO | 2008107918 A1 | 9/2008 | |
| WO | 2018002134 A2 | 1/2018 | |
| WO | 2019130087 A1 | 7/2019 | |

OTHER PUBLICATIONS

Japanese Office Action dated Jun. 6, 2023, issued in corresponding JP Appln. No. 2021569883, 10 pages.

Extended European Search Report dated Dec. 5, 2022, issued in corresponding EP Appln. No. 19931465, 16 pages.

* cited by examiner

CIRCULAR STAPLING DEVICE

BACKGROUND

1. Technical Description

The present disclosure is directed to stapling devices and, more particularly, to circular stapling devices that delay cutting of tissue until after staple formation.

2. Background of Related Art

Conventional manually operated circular stapling devices include an elongate body, a shell assembly that is supported on a distal portion of the elongate body, and an anvil assembly that is movably supported on the distal portion of the elongate body adjacent to the shell assembly. The shell assembly includes a shell housing, a staple cartridge supported on the shell housing, a pusher assembly, and a knife supported on the pusher assembly. The staple cartridge supports a plurality of staples. The pusher assembly includes a staple pushing member that is movable through the staple cartridge to eject the plurality of staples from the staple cartridge through tissue and form the staples against the anvil assembly. The knife is coupled to and movable with the staple pushing member to dissect the tissue clamped between the shell assembly and the anvil assembly during staple formation.

SUMMARY

One aspect of the disclosure is directed to a circular stapling device including a handle assembly, an elongate body, and a shell assembly. The handle assembly includes a firing trigger. The elongate body is supported by the handle assembly and includes a proximal portion and a distal portion. The shell assembly is supported on the distal portion of the elongate body and includes a shell housing defining a cavity, a staple cartridge, a pusher defining a longitudinal bore, a knife carrier, and a knife. The staple cartridge is supported on the shell housing and supports a plurality of staples. The knife carrier is movable within the longitudinal bore of the pusher and the knife is supported on the knife carrier. The pusher is movable within the cavity of the shell housing from a retracted position to an advanced position to eject the plurality of staples from the staple cartridge. The anvil assembly is supported on the distal portion of the elongate body and is movable in relation to the shell assembly between open and clamped positions. The knife carrier is adapted to releasably engage the pusher and is movable between a retracted position and an intermediate position to move the pusher from its retracted position to its advanced position and subsequently movable from its intermediate position to an advanced position independently of the pusher to advance the knife to cut tissue.

In embodiments, the firing trigger is coupled to the knife carrier such that movement of the firing trigger through an actuation stroke moves the knife carrier from its retracted position to its advanced position.

In some embodiments, the firing trigger is manually movable through the actuation stroke.

In certain embodiments, the knife carrier includes at least one tab that is movable from a first position engaged with the pusher to translate distal movement of the knife carrier to distal movement of the pusher to a second position to allow distal advancement of the knife carrier independently of the pusher.

In embodiments, each of the at least one tabs is supported on a resilient arm.

In some embodiments, the resilient arm supporting each of the at least one tabs is supported in cantilevered fashion to the knife carrier.

In certain embodiments, the shell assembly includes a housing that includes at least one longitudinal rib that is positioned to engage the resilient arm supporting each of the at least one tabs to retain each of the at least one tabs in the first position as the pusher is moved towards its advanced position.

In embodiments, one of the pusher and the knife carrier includes a breakable ring and the other of the pusher and the knife carrier includes an annular projection that is positioned to engage the breakable ring.

In some embodiments, the breakable ring is adapted to fracture when the pusher nears its advanced position to facilitate movement of the knife carrier independently of the pusher.

Another aspect of the disclosure is directed to a shell assembly including a shell housing defining a cavity, a staple cartridge, a pusher defining a longitudinal bore, a knife carrier, and a knife. The staple cartridge is supported on the shell housing and supports a plurality of staples. The knife carrier is movable within the longitudinal bore of the pusher and the knife is supported on the knife carrier. The pusher is movable within the cavity of the shell housing from a retracted position to an advanced position to eject the plurality of staples from the staple cartridge. The knife carrier is adapted to engage the pusher and is movable between a retracted position and an intermediate position to move the pusher from its retracted position to its advanced position and subsequently movable from its intermediate position to an advanced position independently of the pusher to advance the knife to cut tissue.

Another aspect of the disclosure is directed to a shell assembly including a shell housing defining a cavity, a staple cartridge, a pusher defining a longitudinal bore, a knife carrier, and a knife. The staple cartridge is supported on the shell housing and supports a plurality of staples. The pusher defines a longitudinal bore and is movable within the cavity of the shell housing from a retracted position to an advanced position to eject the plurality of staples from the staple cartridge. The knife carrier is movable within the longitudinal bore of the pusher and supports the knife, wherein the knife carrier is releasably coupled to the pusher and movable independently of the pusher to cut tissue after staple formation.

BRIEF DESCRIPTION OF THE DRAWINGS

Various embodiments of the disclosed stapling device are described herein below with reference to the drawings, wherein.

DETAILED DESCRIPTION OF EMBODIMENTS

Figure 1:
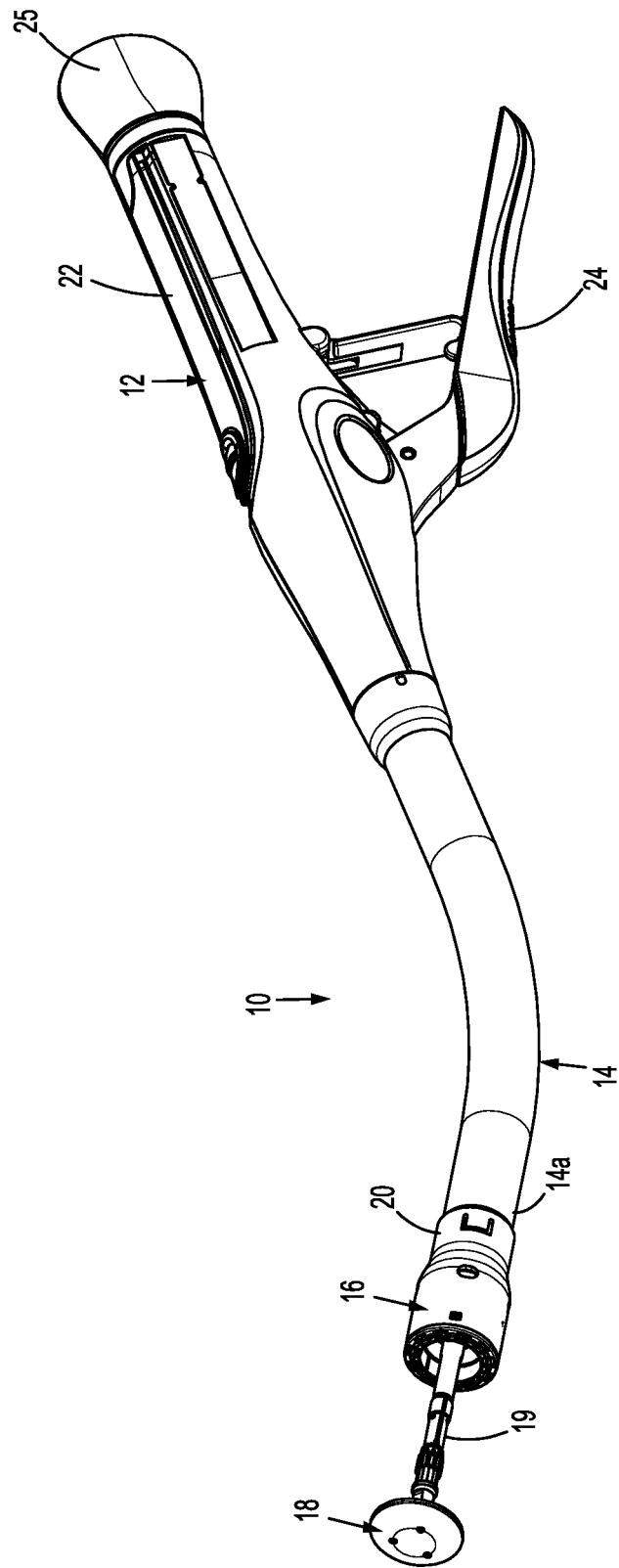
FIG. 1 is a side perspective view of an exemplary embodiment of the disclosed surgical stapling device with an anvil assembly of the stapling device in an open or unclamped position.

The disclosed stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel.

The disclosed circular stapling device is a manually operated stapling device that includes a manually operated trigger that is adapted to allow staple formation to occur prior to cutting of tissue during a single actuation of the firing trigger. The stapling device minimizes stretching and movement of tissue during staple formation to improve staple formation. The stapling device also reduces the amount of force required to move the firing trigger through a firing stroke by separating the staple formation and tissue cutting functions of the stapling device to reduce stress on a clinician's hand during actuation of the stapling device.

FIG. 1 illustrates an exemplary embodiment of the disclosed circular stapling device shown generally as stapling device 10. The stapling device 10 includes a handle assembly 12, an elongate body 14, a shell assembly 16, and an anvil assembly 18 that is supported for movement in relation to the shell assembly 16 between spaced and approximated positions as described below. The anvil assembly 18 has an anvil shaft 19 that is adapted to be releasably coupled to an approximation mechanism (not shown) of the stapling device 10 as is known in the art. The elongate body 14 has a distal portion 14a and a proximal portion 14b. In embodiments, the shell assembly 16 includes a proximal portion 20 that is releasably coupled to the distal portion 14a of the elongate body 14. Alternately, the shell assembly 16 can be fixedly secured to the elongate body portion 14.

The handle assembly 12 includes a stationary grip 22 that supports a firing trigger 24 and an approximation knob 25. The approximation knob 25 is actuable to move the anvil assembly 18 in relation to the shell assembly 16 between open and clamped positions. The firing trigger 24 is movable through an actuation stroke to control operation of various functions of the stapling device 10 including firing of staples from the shell assembly 16 and cutting or coring of tissue.

Figure 2:
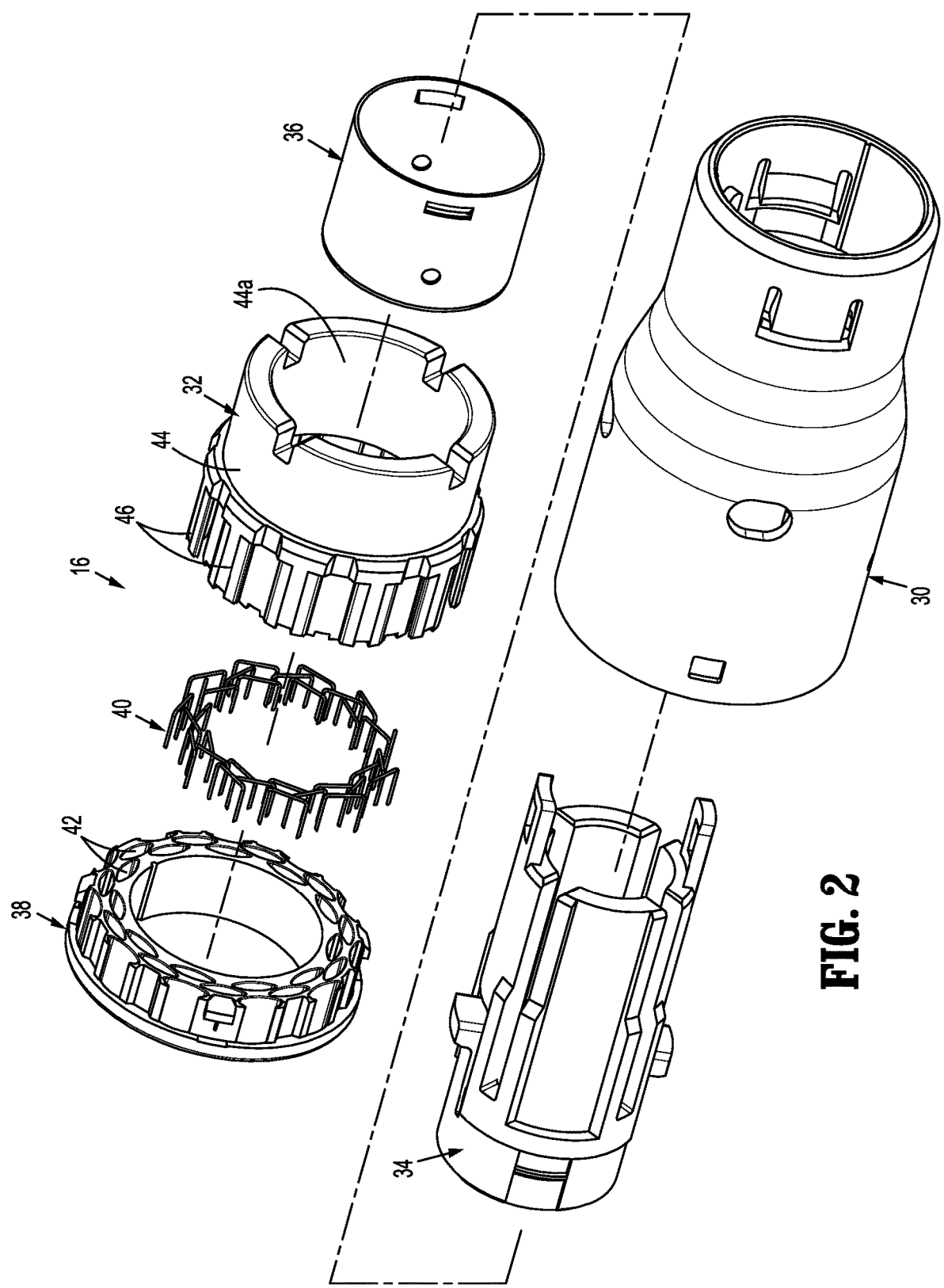
FIG. 2 is a side perspective exploded view of a distal portion of the surgical stapling device shown in FIG. 1.

FIG. 2 illustrates the shell assembly 16 of the stapling device 10 shown in FIG. 1. The shell assembly 16 includes a shell housing 30, a pusher 32, a knife carrier 34, an annular knife 36 supported on the knife carrier 34, a staple cartridge 38, and a plurality of staples 40 supported within the staple cartridge 38. The staple cartridge 38 is annular and defines annular rows of staple pockets 42. Each of the staple pockets 42 supports one of the plurality of staples 40. The pusher 32 includes a body 44 that defines a longitudinal bore 44a and includes a distal portion having a plurality of fingers 46. Each of the plurality of fingers 46 is received within and movable through a respective one of the staple pockets 42 of the staple cartridge 38 to eject the staples 40 from the staple pockets 38 when the pusher 32 is moved within the shell housing 30 from a retracted position to an advanced position.

Figure 3:
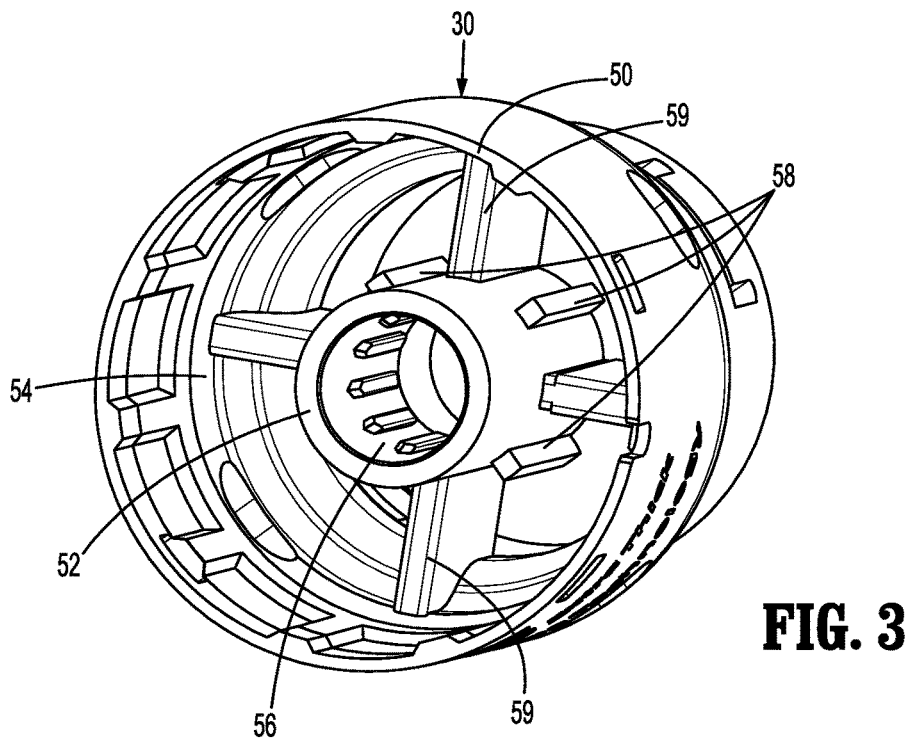
FIG. 3 is a perspective view from the distal end of the shell housing of the distal portion of the stapling device shown in FIG. 2.
Figure 4:
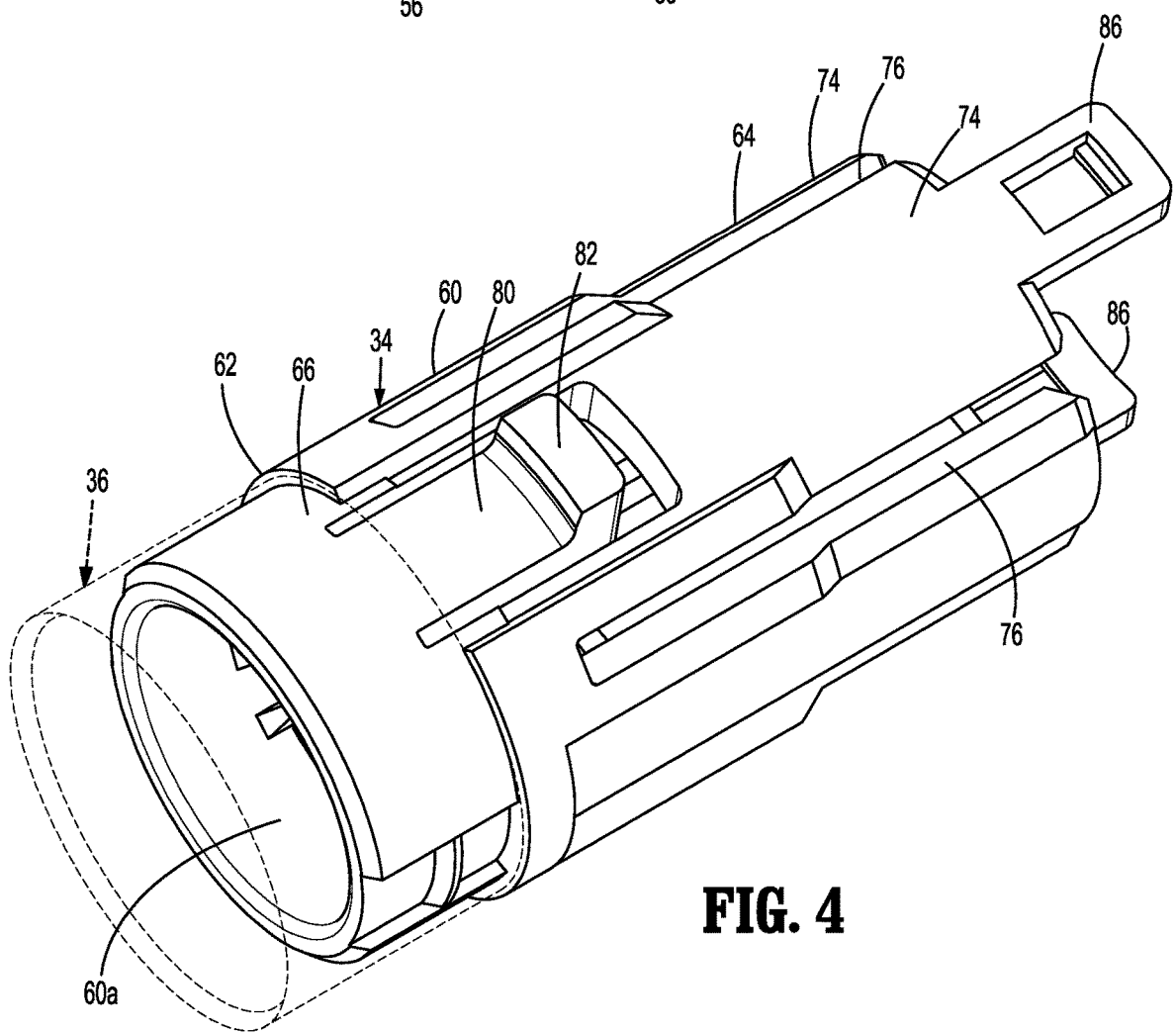
FIG. 4 is a side perspective view of a knife carrier of the distal portion of the stapling device shown in FIG. 2.

FIG. 3 illustrates the shell housing 30 of the shell assembly 16. The shell housing 16 includes an outer housing portion 50 and an inner housing portion 52 that are spaced from each other to define an annular cavity 54. The inner housing portion 52 of the shell housing 30 defines a through bore 56 that receives the anvil shaft 19 (FIG. 1) of the anvil assembly 18 when the anvil assembly 18 is moved to the clamped position to align the anvil assembly 18 with the staple cartridge 38 of the shell assembly 16. The inner housing portion 52 includes an outer surface supporting longitudinal ribs 58 that are positioned within the annular cavity 54 of the shell housing 16. The shell housing 30 also includes struts 59 that extend between the inner housing portion 52 and the outer housing portion 50. The struts 59 confine the knife carrier 34 to longitudinal movement within the shell housing 30 as described in detail below.

The knife carrier 34 is received within the annular cavity 54 of the shell housing 30 and within the pusher 32 and includes an annular body 60. The annular body 60 defines a longitudinal through bore 60a and has a distal portion 62 and a proximal portion 64. In embodiments, the distal portion 62 defines an annular recess 66 that receives the proximal end of the annular knife 36 to secure the knife 36 to the knife carrier 34. The knife 36 may also have tabs 70 (FIG. 2) that engage the knife carrier 34 to further secure the knife 36 to the knife carrier 34. Alternately other securement techniques can be used to secure the knife 36 to the knife carrier 34.

The proximal portion 64 of the annular body 60 of the knife carrier 36 is defined by spaced legs 74 that are separated by longitudinal slots 76. When the knife carrier 34 is received in the annular cavity 54 of the shell housing 30, the longitudinal slots 76 receive the struts 59 of the shell housing 30 to confine the knife carrier 34 to longitudinal movement within the shell housing 30. A proximal portion of the annular body 60 of the knife carrier 34 supports coupling members 86. The coupling members 86 are adapted to engage a drive member (not shown) supported within the elongate body 14 to couple the knife carrier 34 to the firing trigger (FIG. 1).

Figure 5:
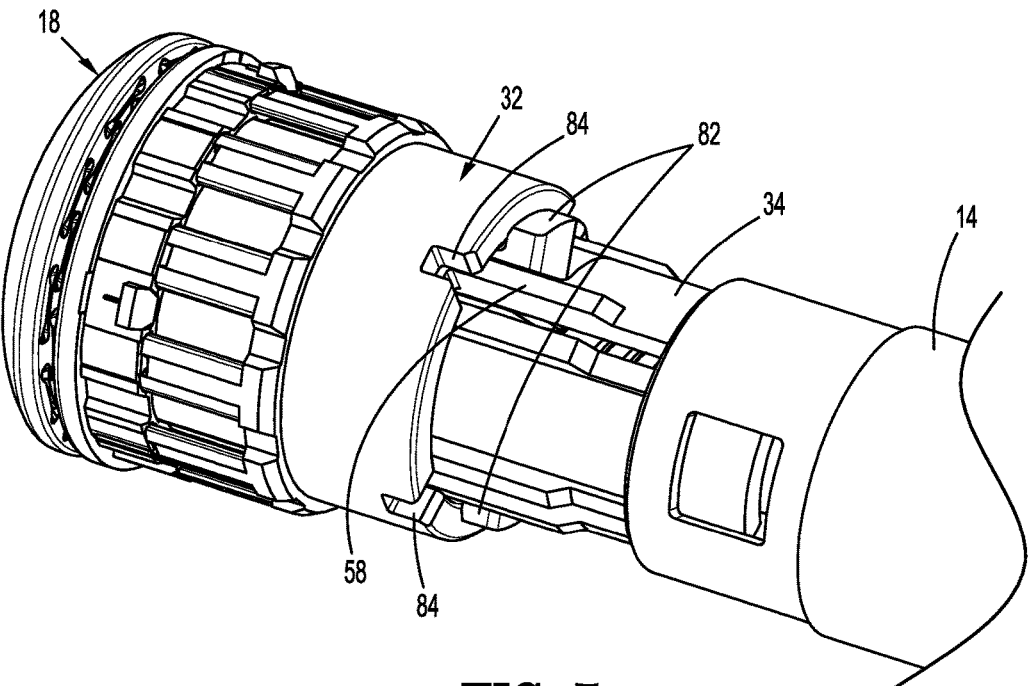
FIG. 5 is a side perspective view of the distal portion of the stapling device shown in FIG. 1 with a shell housing removed and the anvil assembly in a clamped position.
Figure 6:
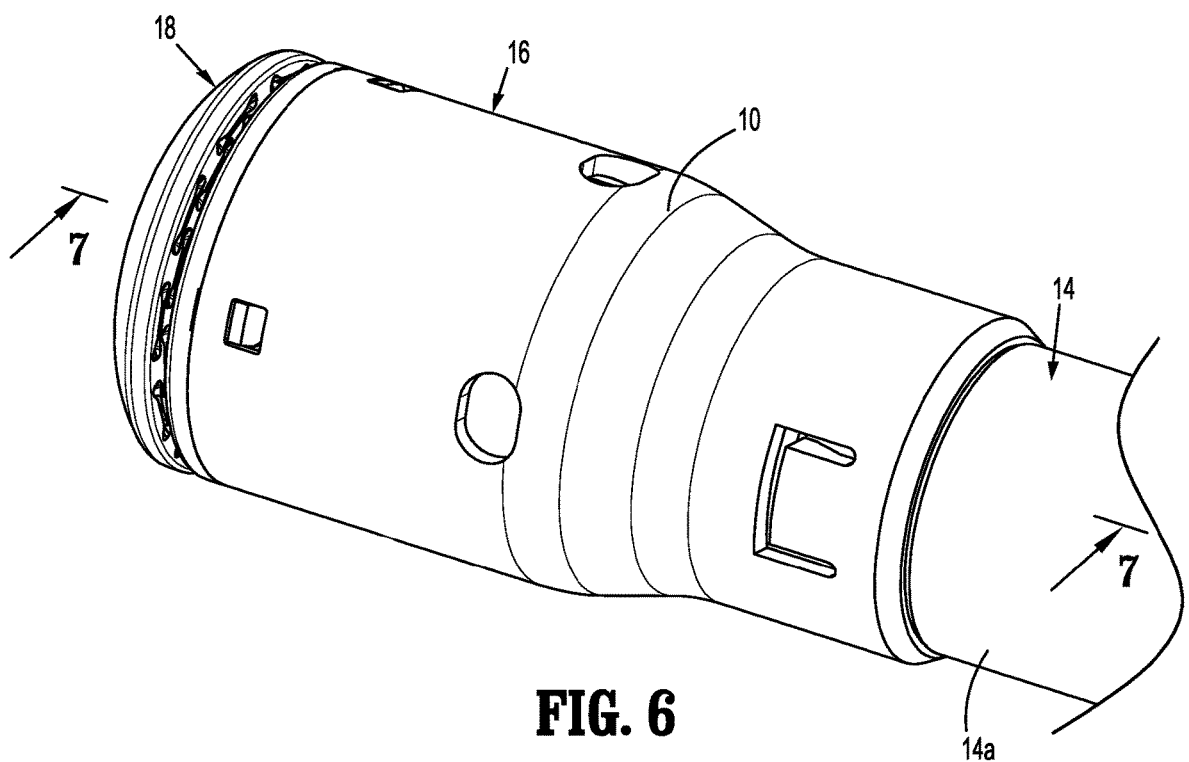
FIG. 6 is a side perspective view of a distal portion of the stapling device shown in FIG. 1 with the anvil assembly in a clamped position.
Figure 7:
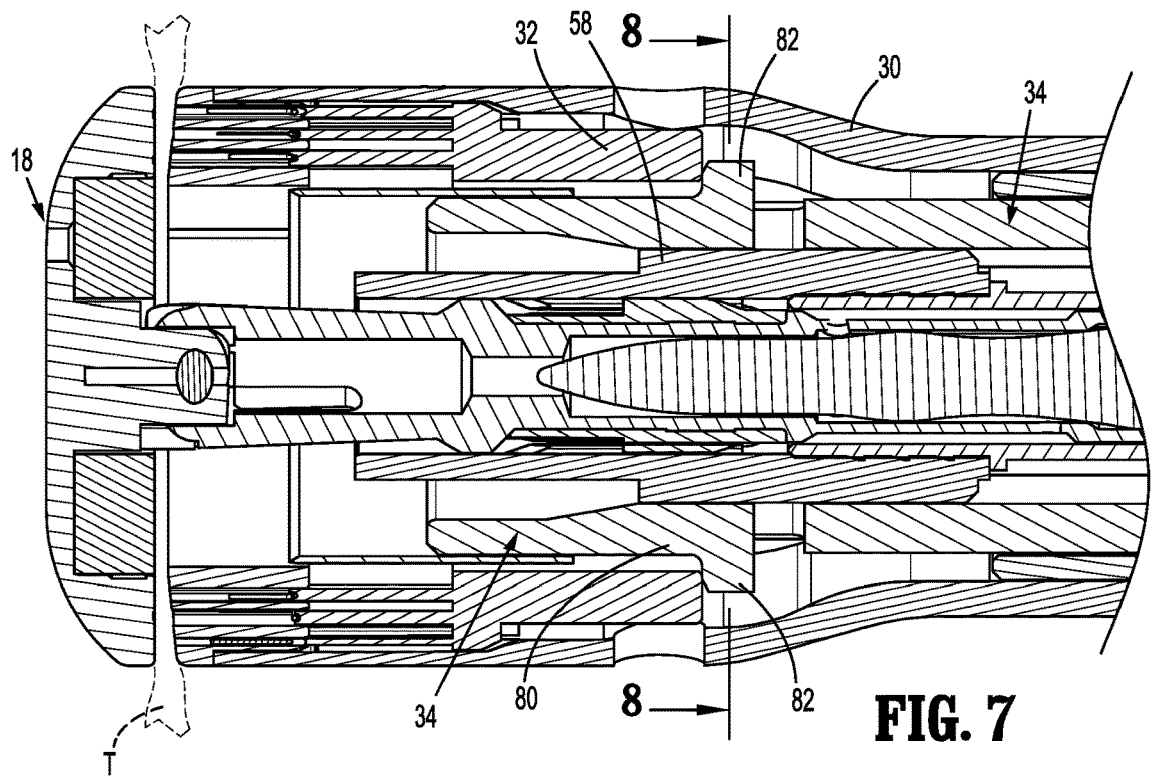
FIG. 7 is a cross-sectional view taken along section line 7-7 of FIG. 3.
Figure 8:
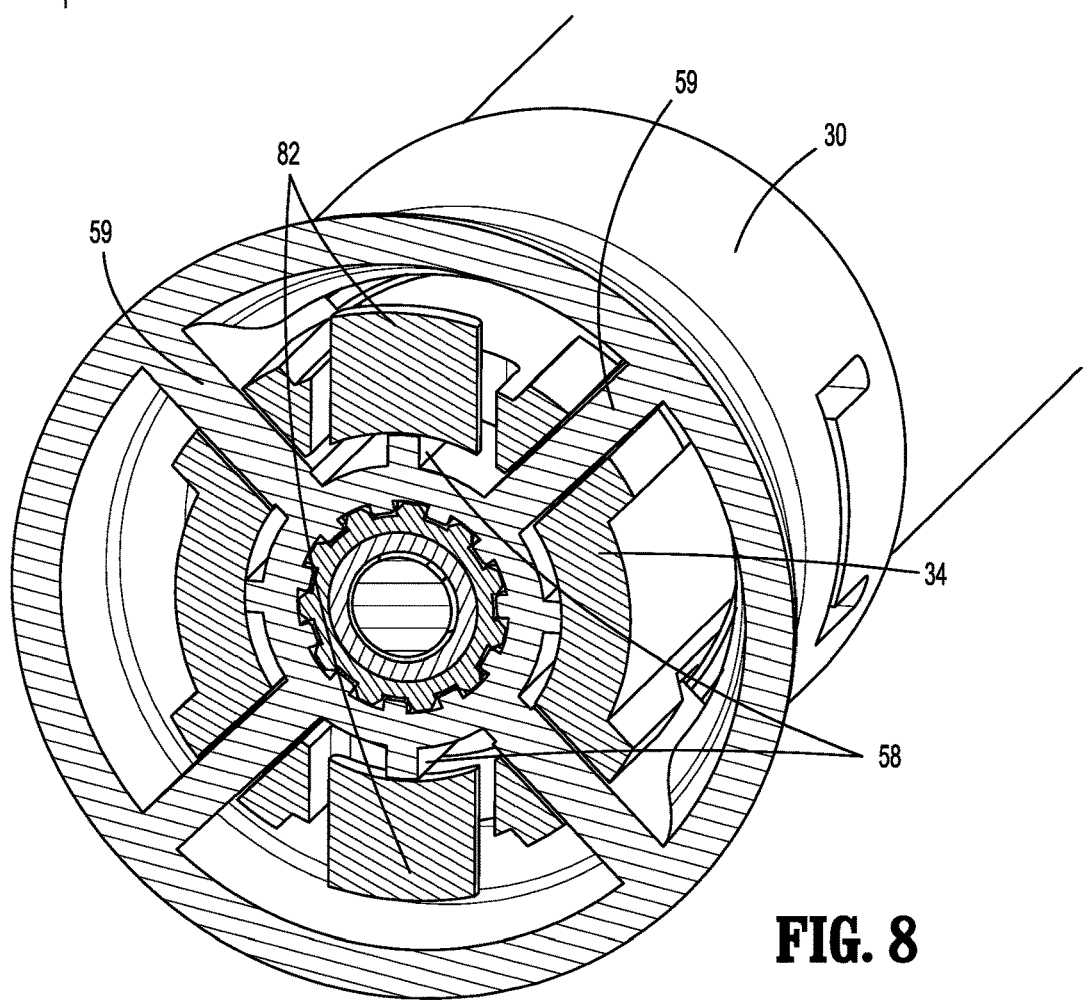
FIG. 8 is a cross-sectional view taken along section line 8-8 of FIG. 7.

FIG. 5 illustrates the distal portion of the knife carrier 34 with the knife carrier received within longitudinal bore 44a of the pusher 32. As illustrated, the annular body 60 of the knife carrier 34 supports one or more resilient cantilevered arms 80. In embodiments, each of the arms 80 has a distal end supported by the annular body 60 and a distal end that supports a tab 82. The tabs 82 extend radially outward from the arms 80 and are positioned to engage a proximal portion of the pusher 32 such that movement of the knife carrier 34 effects distal movement of the pusher 32 within the annular cavity 54 of the shell housing 30 between a retracted position and an advanced position as described in further detail below. The cantilevered arms 80 of the knife carrier 34 are resilient and can flex inwardly into the longitudinal through bore 60a of the knife carrier 34 when the pusher 32 has reached its advanced position to allow the knife carrier 34 to move distally independently of the pusher 32 after staple formation to cut tissue. The tabs 82 may be positioned to engage the proximal end of the pusher 32. Alternately, other configurations are envisioned. As shown in FIG. 5, the proximal portion of the pusher 32 may include elongated slots or notches 84. The notches 84 receive the struts 59 (FIG. 3) of the shell housing 30 to properly align the pusher 32 within the shell housing 30.

FIGS. 5-8 illustrate the distal portion of the stapling device 10 with the anvil assembly 18 in the clamped position about tissue "T" prior to actuation of the firing trigger 24 (FIG. 1). In this position, the knife carrier 34 and the pusher 32 are in their retracted positions within the shell housing 30. The cantilevered arms 80 of the knife carrier 32 are supported on the longitudinal ribs 58 of the inner housing portion 52 of the shell housing 30. When the cantilevered arms 80 are supported on the longitudinal ribs 58, the arms 80 are deformed outwardly from the knife carrier 34 to urge the tabs 82 outwardly into longitudinal alignment and/or engagement with the pusher 32.

Figure 9:
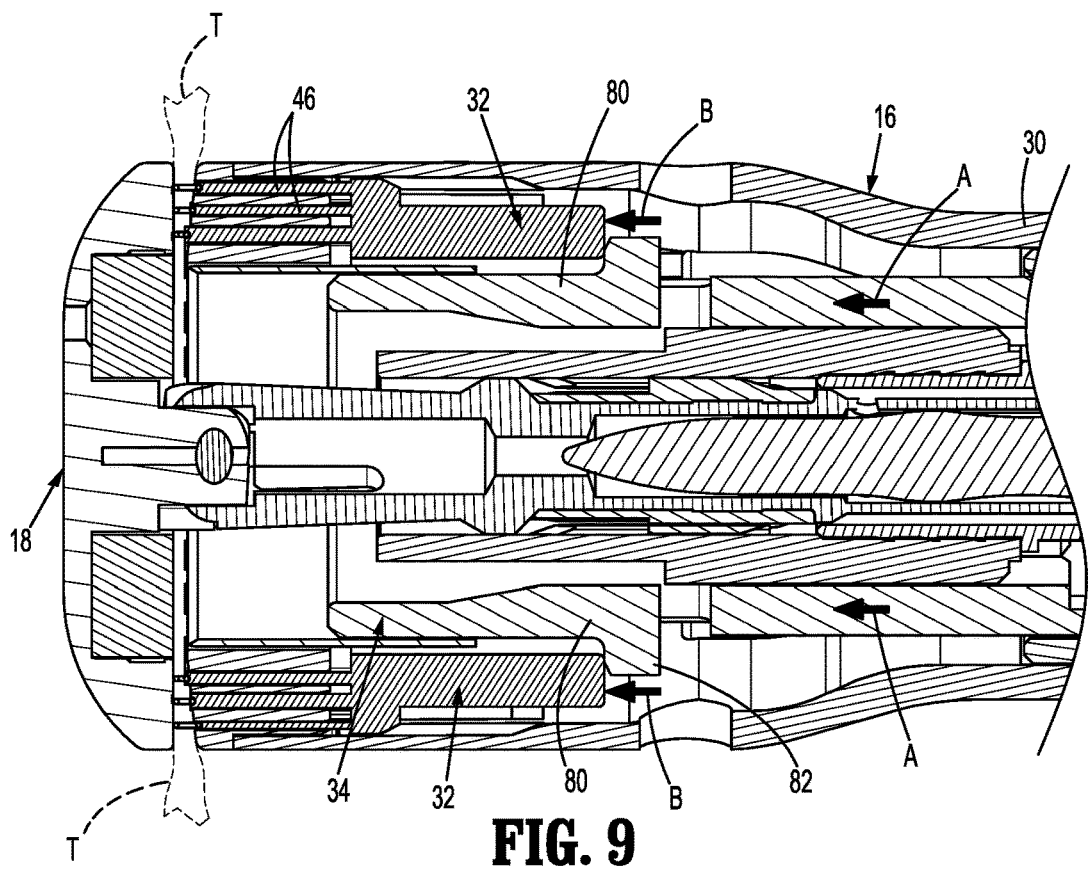
FIG. 9 is a side cross-sectional view through the distal portion of the stapling device shown in FIG. 1 with the anvil assembly in the clamped position and the knife carrier advanced to an intermediate position to form staples.

FIG. 9 illustrates the stapling device 10 with the anvil assembly 18 in the clamped position about the tissue "T" as the firing trigger 24 (FIG. 1) is moved through an actuation stroke and the staples 40 are formed in the tissue "T". Initially, when the firing trigger 24 is actuated, the knife carrier 34 is advanced in the direction indicated by arrows "A". As the knife carrier 34 is advanced, the tabs 82 on the cantilevered arms 80 engage the pusher 32 to advance the pusher 32 with the knife carrier 34 in the direction indicated by arrows "B". As the pusher 32 moves distally within the shell housing 30, the fingers 46 of the pusher 32 pass through the staple pockets 42 of the staple cartridge 38 to advance and form the staples 40 against the anvil assembly 18. In this position, the knife 36 has yet to engage the tissue "T".

Alternately, the knife 36 may be in contact with the tissue "T" as staple formation is completed.

Figure 10:
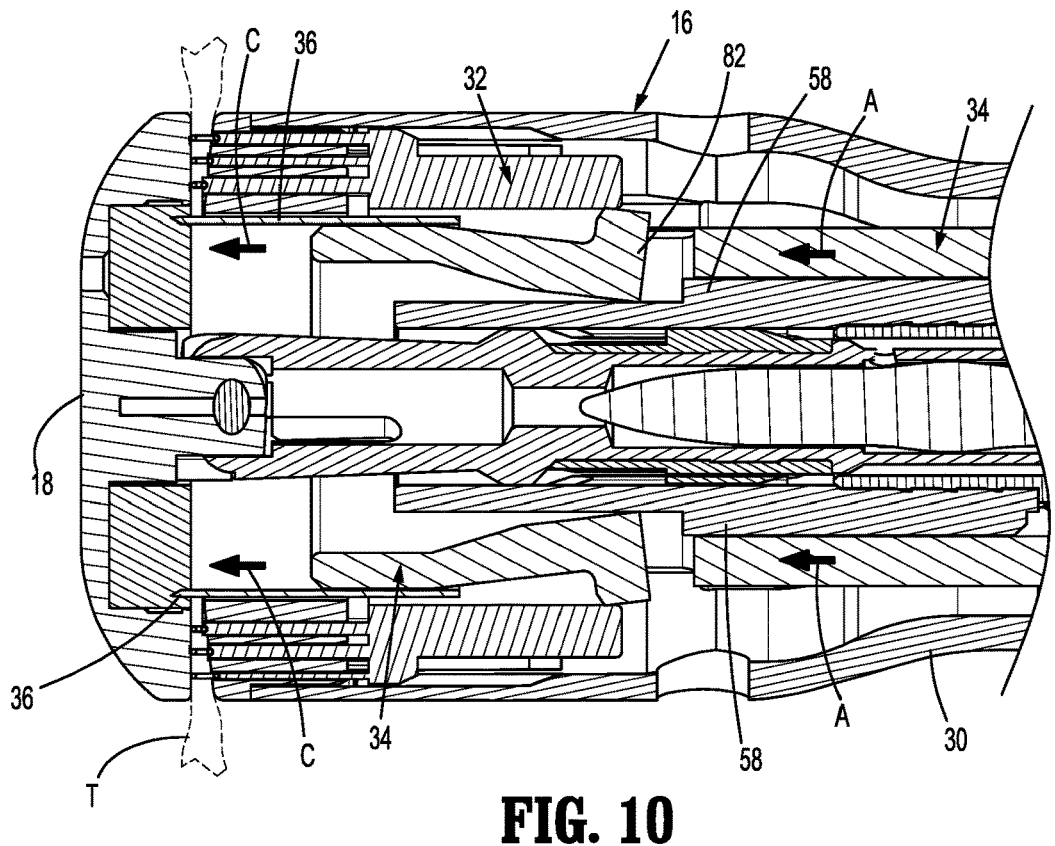
FIG. 10 is a side cross-sectional view through the distal portion of the stapling device shown in FIG. 1 with the anvil assembly in the clamped position and the knife carrier in an advanced position to cut tissue.

As illustrated in FIG. 10, when the knife carrier 34 advances in the direction indicated by arrows "A" to a position in which the cantilevered arms 80 of the knife carrier 34 pass off of distal ends 96 of the longitudinal ribs 58 on the inner housing portion 52 of the shell housing 30, the cantilevered arms 80 move inwardly due to the resilience of the arms 80 such that the tabs 82 disengage from the pusher 32. When this occurs, the knife carrier 34 will advance or move distally independently of the pusher 32 to advance the knife 36 in the direction of arrows "C" to cut the tissue "T". The distal ends of the tabs 82 may include a chamfer 98 to allow engagement between the tabs 82 and the pusher 32 to assist in moving the arms 80 inwardly to facilitate separation of the tabs 82 and the pusher 32.

As discussed briefly above, separating the two functions of the stapling device 10, i.e., staple formation and cutting, allows the forces required to actuate the firing trigger 24 of the stapling device 10 to be reduced and minimizes pulling or stretching of tissue during staple formation to improve staple formation.

FIGS. 12-16 illustrate another exemplary embodiment of the disclosed stapling device 10 (FIG. 1) which is similar to the embodiment described above with the exception of modifications to the pusher 132 and the knife carrier 134 which are described in further detail below.

Figure 11:
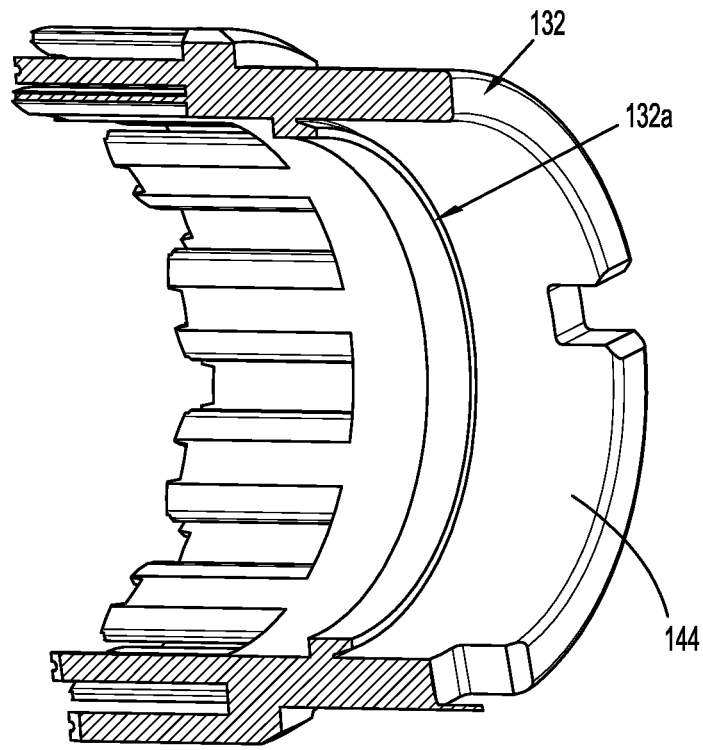
FIG. 11 is a side perspective cross-sectional view an alternate embodiment of the staple pusher of the stapling device shown in FIG. 1.
Figure 12:
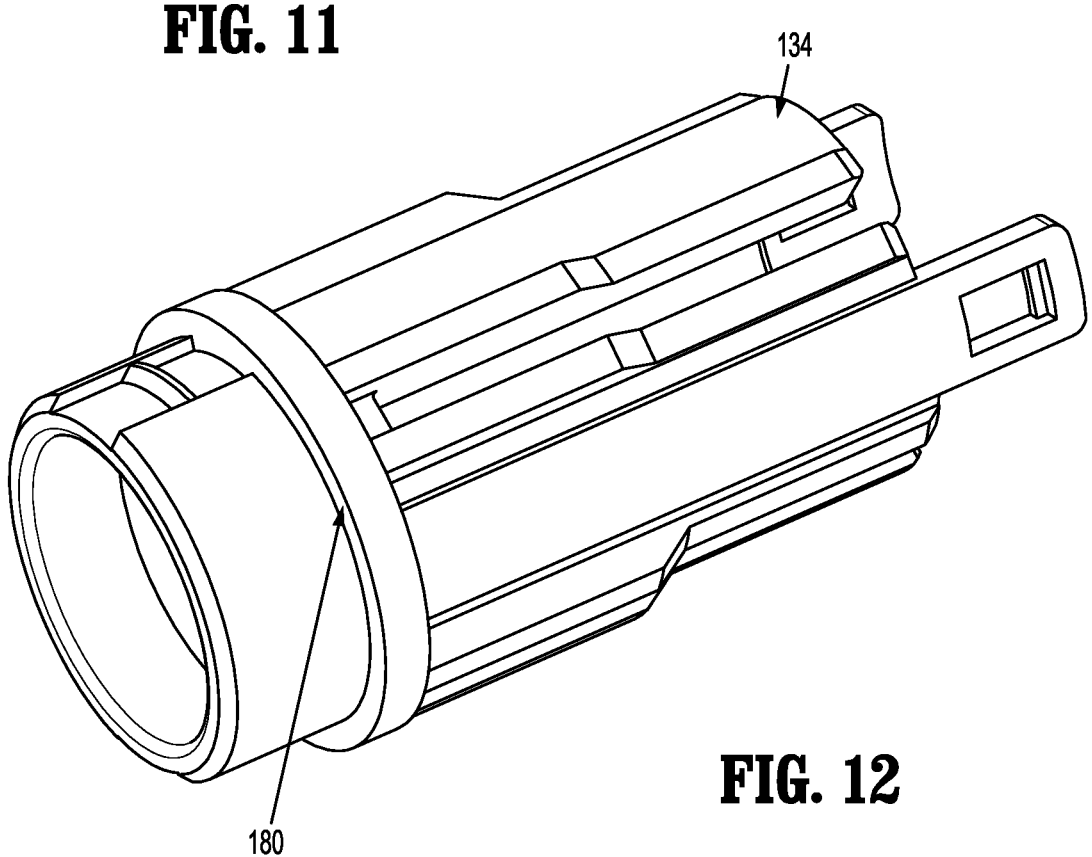
FIG. 12 is a side perspective view of the knife carrier of the stapling device shown in FIG. 1.

The pusher 132 is substantially identical to the pusher 32 (FIG. 2) except that the inner wall of the pusher 32 includes a frangible or breakable ring 132a (FIG. 11) that projects into the longitudinal bore 144a of the pusher 132. In addition, the knife carrier 134 is substantially similar to the knife carrier 34 except that the cantilevered arms 80 are eliminated and a projection, such as an annular ring 180 (FIG. 12), is formed on the distal portion 162 of the knife carrier 134.

Figure 13:
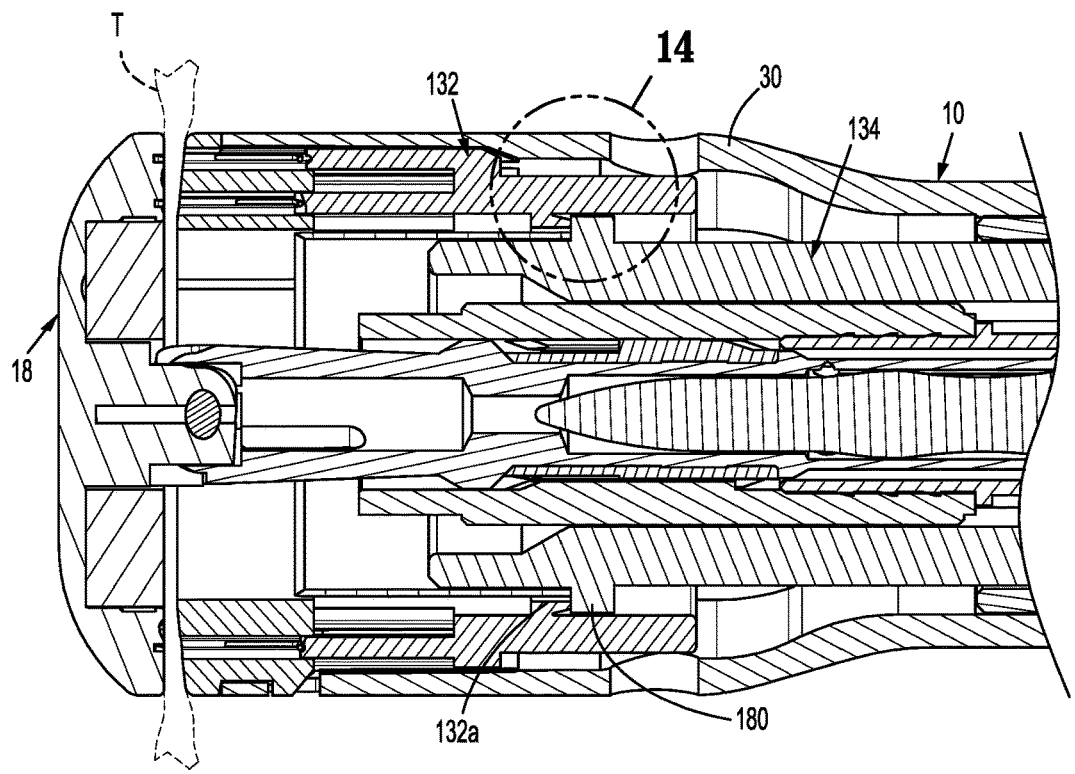
FIG. 13 is a side cross-sectional view through a distal portion of the stapling device shown in FIG. 1 including the pusher of FIG. 11 and the knife carrier of FIG. 12 in the clamped position and the knife carrier in the retracted position.
Figure 14:
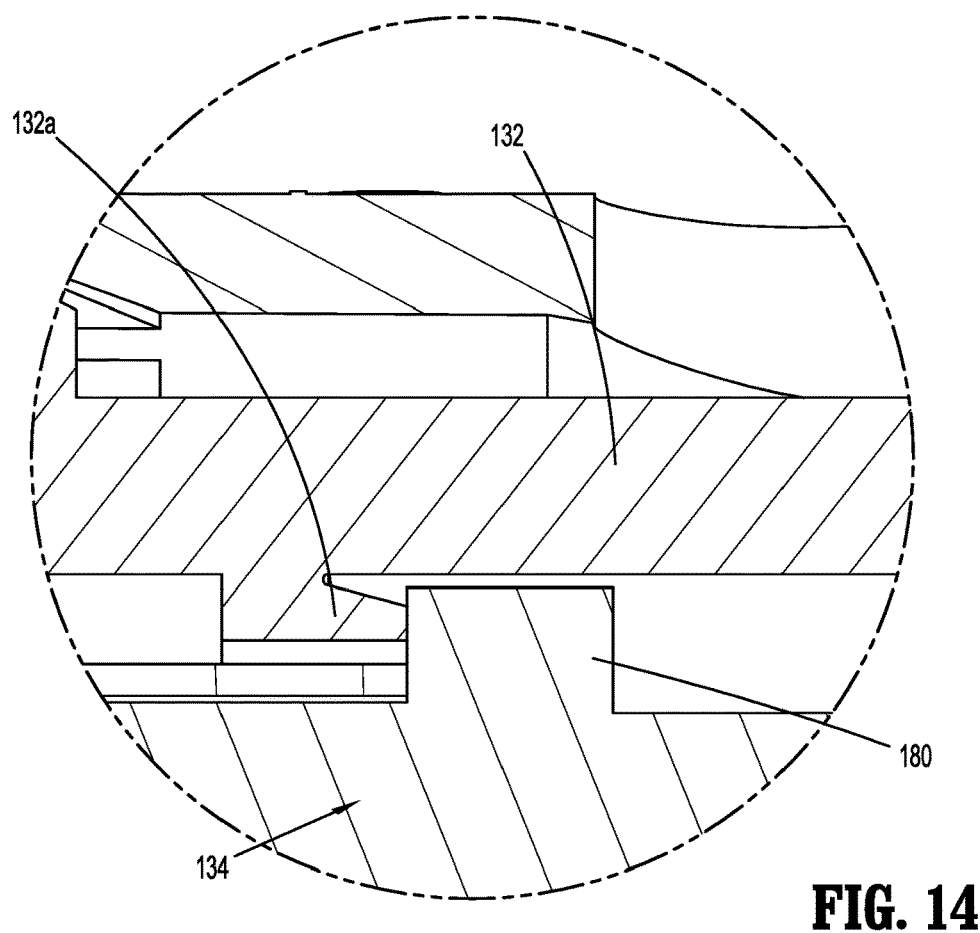
FIG. 14 is an enlarged view of the indicated area of detail shown in FIG. 13.

FIG. 13 illustrates the distal portion of the stapling device 10 (FIG. 1) with the anvil assembly 18 in the clamped position about tissue "T" prior to actuation of the firing trigger 24 (FIG. 1). In this position, the knife carrier 134 and the pusher 132 are in their retracted positions within the shell housing 30. The projection on the knife carrier 134, e.g., annular ring 180, is positioned immediately proximal to and in alignment with the breakable ring 132a of the pusher 132. Although the annular ring 180 of the knife carrier 134 is shown engaged with the breakable ring 132a, the two components need only be aligned with each other prior to actuation of the firing trigger 24 (FIG. 1).

Figure 15:
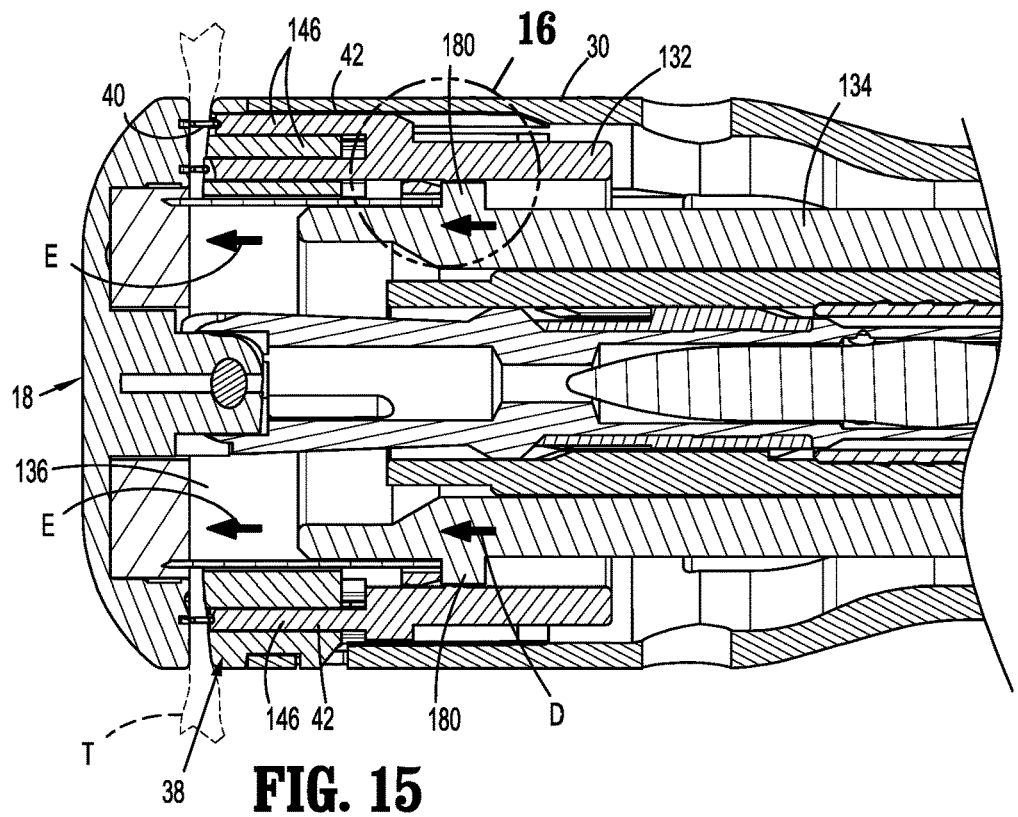
FIG. 15 is a side cross-sectional view through a distal portion of the stapling device shown in FIG. 1 with the anvil assembly in the clamped position and the knife carrier advanced to a position in which the staples are formed and tissue begins to be cut.
Figure 16:
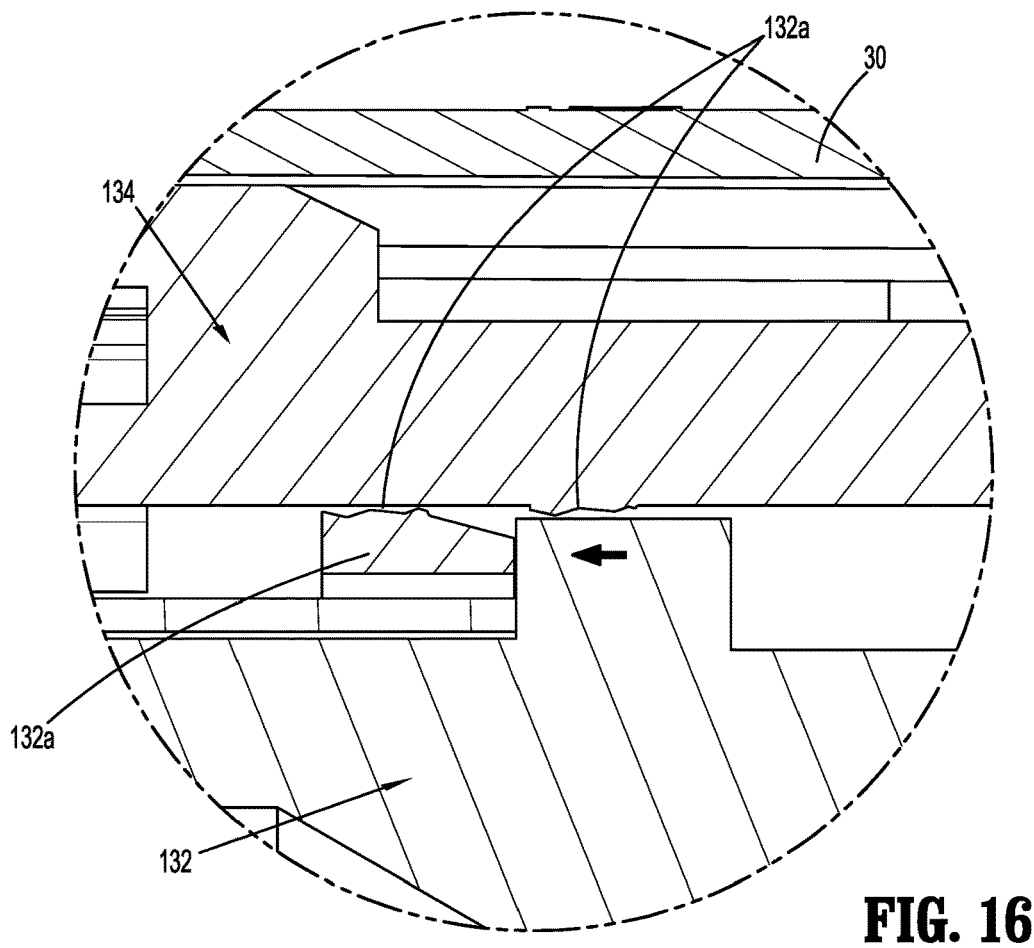
FIG. 16 is an enlarged view of the indicated area of detail shown in FIG. 15.

FIGS. 15 and 16 illustrate the stapling device 10 with the anvil assembly 18 in the clamped position about the tissue "T" as the firing trigger 24 (FIG. 1) is moved through an actuation stroke. Initially, when the firing trigger 24 (FIG. 1) is actuated the knife carrier 134 is advanced in the direction indicated by arrows "D". As the knife carrier 134 is advanced, the annular ring 180 on the knife carrier 134 engages the breakable ring 132a on the pusher 132 to advance the pusher 132 with the knife carrier 34 in the direction indicated by arrows "D". As the pusher 132 moves distally within the shell housing 30, the fingers 146 of the pusher 132 passes through the staple pockets 42 of the staple cartridge 38 to advance and form the staples 40 against the anvil assembly 18. In this position, the knife 136 has yet to engage the tissue "T". Alternately, the knife 136 may be in contact with the tissue "T" as staple formation is completed.

When the staple formation is completed, advancement of the pusher 132 is obstructed via engagement between the staple cartridge 38 and the pusher 132. When this occurs, the force applied to the breakable ring 132a of the pusher 132 by the annular ring 180 of the knife carrier 132 increase beyond a threshold force and the breakable ring 132a is sheared from the inner wall of the pusher 132 to allow the knife carrier 132 to move distally independently of the pusher 132 in the direction indicate by arrows "E" to cut the tissue "T".

As discussed briefly above, separating the two functions of the stapling device 10, i.e., staple formation and cutting, allows the forces required to actuate the firing trigger 24 of the stapling device 10 to be reduced and minimizes pulling or stretching of tissue during staple formation to improve staple formation.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A circular stapling device comprising:
   a handle assembly including a firing trigger;
   an elongate body supported by the handle assembly, the elongate body having a proximal portion and a distal portion;
   a shell assembly supported on the distal portion of the elongate body, the shell assembly including a shell housing defining a cavity, a staple cartridge supported on the shell housing, a pusher defining a longitudinal bore, a knife carrier movable within the longitudinal bore, and a knife supported on the knife carrier, the staple cartridge supporting a plurality of staples and the pusher being movable within the cavity of the shell housing from a retracted position to an advanced position to eject the plurality of staples from the staple cartridge; and
   an anvil assembly supported on the distal portion of the elongate body and being movable in relation to the shell assembly between open and clamped positions;
   wherein the knife carrier engages the pusher and is movable between a retracted position and an intermediate position to move the pusher from its retracted position to its advanced position and subsequently movable from its intermediate position to an advanced position independently of the pusher to advance the knife to cut tissue.

2. The circular stapling device of claim 1, wherein the firing trigger is coupled to the knife carrier such that movement of the firing trigger through an actuation stroke moves the knife carrier from its retracted position to its advanced position.

3. The circular stapling device of claim 2, wherein the firing trigger is manually movable through the actuation stroke.

4. The circular stapling device of claim 1, wherein the knife carrier includes at least one tab, the at least one tab being movable from a first position engaged with the pusher to translate distal movement of the knife carrier to distal movement of the pusher, to a second position to allow distal advancement of the knife carrier independently of the pusher.

5. The circular stapling device of claim 4, wherein each of the at least one tabs is supported on a resilient arm.

6. The circular stapling device of claim 5, wherein the resilient arm supporting each of the at least one tabs is supported in cantilevered fashion to the knife carrier.

7. The circular stapling device of claim 5, wherein the shell assembly includes a housing that includes at least one longitudinal rib, the at least one longitudinal rib being positioned to engage the resilient arm supporting each of the at least one tabs to retain each of the at least one tabs in the first position as the pusher is moved towards its advanced position.

8. The circular stapling device of claim 1, wherein one of the pusher and the knife carrier includes a breakable ring and the other of the pusher and the knife carrier includes an annular projection that is positioned to engage the breakable ring.

9. The circular stapling device of claim 8, wherein the breakable ring is adapted to fracture when the pusher nears its advanced position to facilitate movement of the knife carrier independently of the pusher.

10. A shell assembly comprising:
    a shell housing defining a cavity;
    a staple cartridge supported on the shell housing, the staple cartridge supporting a plurality of staples;
    a pusher defining a longitudinal bore;
    a knife carrier movable within the longitudinal bore of the pusher; and
    a knife supported on the knife carrier;
    wherein the pusher is movable within the cavity of the shell housing from a retracted position to an advanced position to eject the plurality of staples from the staple cartridge, and the knife carrier engages the pusher and is movable between a retracted position and an intermediate position to move the pusher from its retracted position to its advanced position and subsequently movable from its intermediate position to an advanced position independently of the pusher to advance the knife to cut tissue.

11. The shell assembly of claim 10, wherein the firing trigger is coupled to the knife carrier such that movement of the firing trigger through an actuation stroke moves the knife carrier from its retracted position to its advanced position.

12. The shell assembly of claim 10, wherein the knife carrier includes at least one tab, the at least one tab being movable from a first position engaged with the pusher to translate distal movement of the knife carrier to distal movement of the pusher, to a second position to allow distal advancement of the knife carrier independently of the pusher.

13. The shell assembly of claim 12, wherein each of the at least one tabs is supported on a resilient arm.

14. The shell assembly of claim 13, wherein the resilient arm supporting each of the at least one tabs is supported in cantilevered fashion to the knife carrier.

15. The shell assembly of claim 13, wherein the shell assembly includes a housing that includes at least one longitudinal rib, the at least one longitudinal rib being positioned to engage the resilient arm supporting each of the at least one tabs to retain each of the at least one tabs in the first position as the pusher is moved towards its advanced position.

16. The shell assembly of claim 10, wherein one of the pusher and the knife carrier includes a breakable ring and the other of the pusher and the knife carrier includes an annular projection that is positioned to engage the breakable ring.

17. The shell assembly of claim 16, wherein the breakable ring is adapted to fracture when the pusher nears its advanced position to facilitate movement of the knife carrier independently of the pusher.

18. A shell assembly comprising:
a shell housing defining a cavity;
a staple cartridge supported on the shell housing, the staple cartridge supporting a plurality of staples;
a pusher defining a longitudinal bore, the pusher being movable within the cavity of the shell housing from a retracted position to an advanced position to eject the plurality of staples from the staple cartridge;
a knife carrier movable within the longitudinal bore of the pusher; and
a knife supported on the knife carrier;
wherein the knife carrier is releasably coupled to the pusher and movable independently of the pusher to cut tissue after staple formation.

19. The shell assembly of claim 18, wherein the knife carrier includes at least one tab, the at least one tab being movable from a first position engaged with the pusher to translate distal movement of the knife carrier to distal movement of the pusher, to a second position to allow distal advancement of the knife carrier independently of the pusher.

20. The shell assembly of claim 18, wherein one of the pusher and the knife carrier includes a breakable ring and the other of the pusher and the knife carrier includes an annular projection that is positioned to engage the breakable ring.

* * * * *